United States Patent
Shim et al.

(10) Patent No.: US 7,346,458 B2
(45) Date of Patent: Mar. 18, 2008

(54) GENOTYPING METHOD USING DNA CHIP

(75) Inventors: Hyeong-sop Shim, Gyeonggi-do (KR); Tae-sung Park, Seoul (KR); Jae-shick Yang, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 568 days.

(21) Appl. No.: 10/763,694

(22) Filed: Jan. 23, 2004

(65) Prior Publication Data

US 2005/0089877 A1     Apr. 28, 2005

(30) Foreign Application Priority Data

Jan. 25, 2003  (KR)  ............... 10-2003-0005025

(51) Int. Cl.
G06F 19/00   (2006.01)

(52) U.S. Cl. ............... 702/19; 435/6; 702/23; 703/2; 706/13

(58) Field of Classification Search ............ None
See application file for complete search history.

(56) References Cited

U.S. PATENT DOCUMENTS

| | | | |
|---|---|---|---|
| 6,027,880 A | 2/2000 | Cronin et al. | 435/6 |
| 6,300,063 B1 | 10/2001 | Lipshutz et al. | 435/6 |
| 6,303,301 B1 * | 10/2001 | Mack | 435/6 |

FOREIGN PATENT DOCUMENTS

| | | |
|---|---|---|
| KR | 2003-0020232 | 3/2003 |
| KR | 2003-0072709 | 9/2003 |

OTHER PUBLICATIONS

Office Action of Korean Patent Office regarding corresponding Korean Patent Application No. 10-2003-0005025, dated Dec. 23, 2004.
"Applied Logistic Regression"; Second Edition; Authors: David W. Hosmer and Stanley Lemeshow; Wiley Series in Probability and Statistics; pp. 1-30, 2000.

* cited by examiner

*Primary Examiner*—Carolyn L. Smith
(74) *Attorney, Agent, or Firm*—Cantor Colburn LLP

(57) ABSTRACT

A robust genotyping method using a DNA chip is provided. In the DNA chip used in the genotyping method, optimal probe pairs of a wild-perfect match probe and a mutant-perfect match probe are immobilized for each mutation site on a substrate. The method includes setting up a genotyping algorithm using data obtained from hybridization of an identified standard nucleic acid to the DNA chip, and genotyping an unknown target nucleic acid by substituting input vectors that are calculated from hybridization of the target nucleic acid to the DNA chip into the genotyping algorithm. The results of genotyping the target nucleic acid using the optimal probe pairs for each mutation site are statistically robust to errors.

14 Claims, 6 Drawing Sheets

FIG. 8

GENOTYPING METHOD USING DNA CHIP

This application claims the priority of Korean Patent Application No. 2003-5025, filed on Jan. 25, 2003, in the Korean Intellectual Property Office, the disclosure of which is incorporated herein in its entirety by reference.

BACKGROUND OF THE INVENTION

1. Field of the Invention

The present invention relates to a robust method of identifying whether a target nucleic acid is a wild type or a mutant type using a DNA chip.

2. Description of the Related Art

The most common genotyping method is to identify sequences using sequencing machine. This method is accurate but is unsuitable for genotyping a number of samples at a time and leads to a low yield.

Recent disclosures of DNA chips that can simultaneously identify various genotypes at different positions, such as U.S. Pat. Nos. 6,027,880 and 6,300,063, are attracting a lot of interest. The DNA chips disclosed in the patents utilize tiled arrays of from 9 to 24-mer oligonucleotide probes at non-mutation sites and A, C, G, and T at mutation sites. Since all possible base combinations are used for a tiled array of probes mobilized at and near mutation sites, the number of required probes increases four times whenever one more tiled array site is required.

However, such a tiled array includes redundant probes for an identified target nucleic acid. In addition, the tiled array method cannot applied to detect mutations, for example, by insertion or deletion. Since a tiled array includes numerous probes having similar sequences and a fixed length, it is difficult to interpret the results of genotyping a particular locus using such a tiled array, and the manufacturing costs of DNA chips rise. For example, if the hybridization intensity of a wild-perfect match probe or a mutant-perfect match probe is lower than the hybridization intensity of the other mismatch probes, a genotyping error occurs and it is not possible to prove a cross-hybridization effect. Also, the fixed length of the probes in the tiled array hinders optimal hybridization with a particular nucleic acid.

SUMMARY OF THE INVENTION

The present invention provides a genotyping method that is immune from errors in discrimination and utilizes a minimum number of probes that have various lengths.

The present invention also provides a DNA chip used in the above genotyping method.

In one aspect of the present invention, there is provided a genotyping method using a DNA chip on which an optimal probe pair of a wild type-perfect match probe and a mutant type-perfect match probe are immobilized for each mutation site. At least two replicates of optimal probe pairs may be immobilized for each mutation site of the DNA chip.

The genotyping method may include setting up a genotyping algorithm using data obtained from hybridization of an identified standard nucleic acid to the DNA chip, and genotyping an unknown target nucleic acid by substituting an input vector that are calculated from hybridization of the target nucleic acid to the DNA chip into the genotyping algorithm. The genotyped results may be corrected based on cross-hybridization data of the probe pair for each mutation site.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Embodiments of a genotyping method and a DNA chip used therein according to the present invention will be described with reference to the appended drawings. This invention may, however, be embodied in many different forms and should not be construed as being limited to the embodiments set fourth herein; rather, these embodiments are provided so that this disclosure will be thorough and complete, and will fully convey the concept of the invention to those skilled in the art. The scope of the present invention is defined only by the appended claims. In the drawings, like reference numerals are used to refer to like elements throughout.

Throughout the specification, the term "DNA chip" means a microarray of a number of nucleic acid probes. Nucleic acids mean nucleotides that include pyrimidine bases, including cytosine, thymine, and uracil, and purine bases, including adenine and guanine, and polymers (also referred to as polynucleotides) or oligomers (also referred to as oligonucleotides) of the nucleotides. Examples of DNA chips include cDNA chips with at least 500 bp probes and oligonuclotide chips with polygonucleotide probes.

The term "standard nucleic acid" used throughout the specification means a nucleic acid that has an identified genotype. The term "target nucleic acid" means a nucleic acid of interest that has an unknown genotype. The target nucleic acid may be an oligonucleotide or polynucleotide of RNA or DNA. The term "probe" means a nucleic acid used to genotype the target nucleic acid. Hereinafter, a probe that perfectly matches a wild type gene will be referred to as a wild type-perfect match probe (wp), and a probe that perfectly matches a mutant gene will be referred to as a mutant type-perfect match probe (mp).

In the flowcharts, blocks outlined by dashed lines denote optional processing steps.

Figure 1:
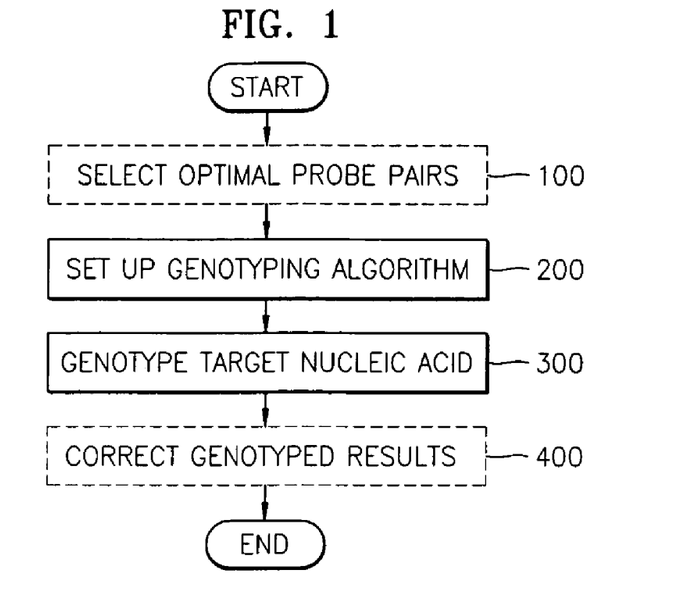
FIG. 1 is a flowchart of a genotyping method according to the present invention.

Referring to FIG. 1, a robust genotyping method according to an embodiment of the present invention includes setting up a genotyping algorithm (step 200) and genotyping a target nucleic acid (step 300). Optionally, the genotyping method according to the present invention may further include selecting optimal probe pairs (step 100) before step 200 and correcting the genotyped results (step 400) after step 300. In the genotyping method according to the present invention, a DNA chip in which optimal probe pairs of a wp probe and a mp probe are arranged at mutation sites is utilized to genotype the target nucleic acid. Therefore, there is no need to lay unnecessary probes on the chip. In addition, it is simple to interpret the results, and errors resulting from cross-hybridization can be easily corrected, and the manufacturing costs of the DNA chip are low. The genotyping method according to the present invention may be applied to mutants, for example, by insertion or deletion. The genotyping method according to the present invention will be described step by step.

Optimal Probe Pair Selection

Figure 2:
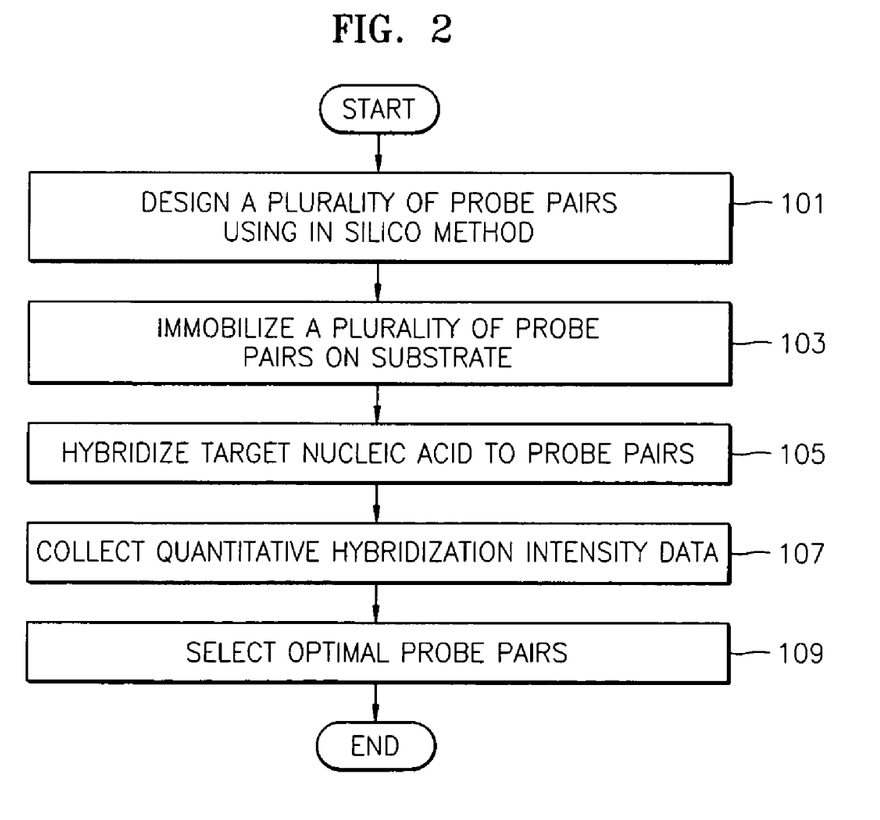
FIG. 2 is a flowchart of the step of screening optimal probe pairs in the genotyping method according to the present invention.

FIG. 2 is a detailed flowchart of the screening of optimal probes pairs in step 100 in FIG. 1. In particular, a plurality of wp probes and a plurality of mp probes for each mutation site are designed using an in silico method (step 101). The wp probes and mp probes may have the same length or different lengths. In other words, there is no limitation to the length of the wp and mp probes provided that they are same strand. The wp and mp probes are paired into a plurality of wp-mp pairs and immobilized on a substrate to form a complete chip for screening optimal probe pairs (step 103). The immobilization of the wp-mp pairs on the substrate may be achieved by one of various methods that are known to those of ordinary skill in the field. As an example, the wp-mp pairs may be immobilized on the chip according to a method disclosed in Korean Patent Application No. 2001-53687 filed by the same applicant as the present invention, incorporated herein by reference in its entirety.

Next, a target nucleic acid is hybridized to the chip that is manufactured to screen optimal probe pairs (step 105). This hybridization process may be carried out by one of various methods that are known to those of ordinary skill in the field. After hybridization, quantitative hybridisation intensity data are collected by means of a scanner (step 107). A number of quantitative hybridization intensity data are collected using a plurality of optimal probe pair screening chips. Finally, optimal wp-mp pairs for the respective mutation sites are selected based on the quantitative hybridization intensity data (step 109). All possible combinations of wp-mp pair are tested for the optimal wp-mp pair per mutation site. Equation (1) below may be used to select the optimal wp-mp pairs for the respective mutation sites.

$$\{\text{Mean}(\ln(r^{wt})) - 2\ SD(\ln(r^{wt}))/\sqrt{N^{wt}}\} - \{\text{Mean}(\ln(r^{mt})) + 2SD(\ln(r^{mt}))/\sqrt{N^{mt}}\} \quad (1)$$

In equation (1) above, N denotes the number of times hybridization of the target nucleic acid has been performed; $r^{wt}$ is the ratio between the hybridization intensity of a wild type standard nucleic acid to the wp probe and the hybridization intensity of the wild type standard nucleic acid to the mp probe; $r^{mt}$ is the ratio between the hybridization intensity of a mutant type standard nucleic acid to the wp probe and the hybridization intensity of the mutant type standard nucleic acid to the mp probe; and Means and SD denote the mean value and standard deviation of N ln(r) values, respectively, which are obtained by hybridizing the standard nucleic acid to the DNA chip N times. The median of N ln(r) values instead of the mean value may be used.

A pair of wp-mp probes that has the largest value among the values calculated using equation (1) above is selected as the optimal probe pair. The optimal probe pair may be selected using a method disclosed in Korean Patent Application No. 02-118771 filed on Mar. 6, 2002 by the same applicant as the present invention, incorporated herein by reference in its entirety.

It will be appreciated that this step of screening out the optimal probe pairs may be not conducted when there is a known optimal probe pair for each mutation site.

Genotyping Algorithm Set up

After the optimal probe pairs for the respective mutation sites are selected according to the procedure of FIG. 2, a genotyping algorithm is set up.

Figure 3:
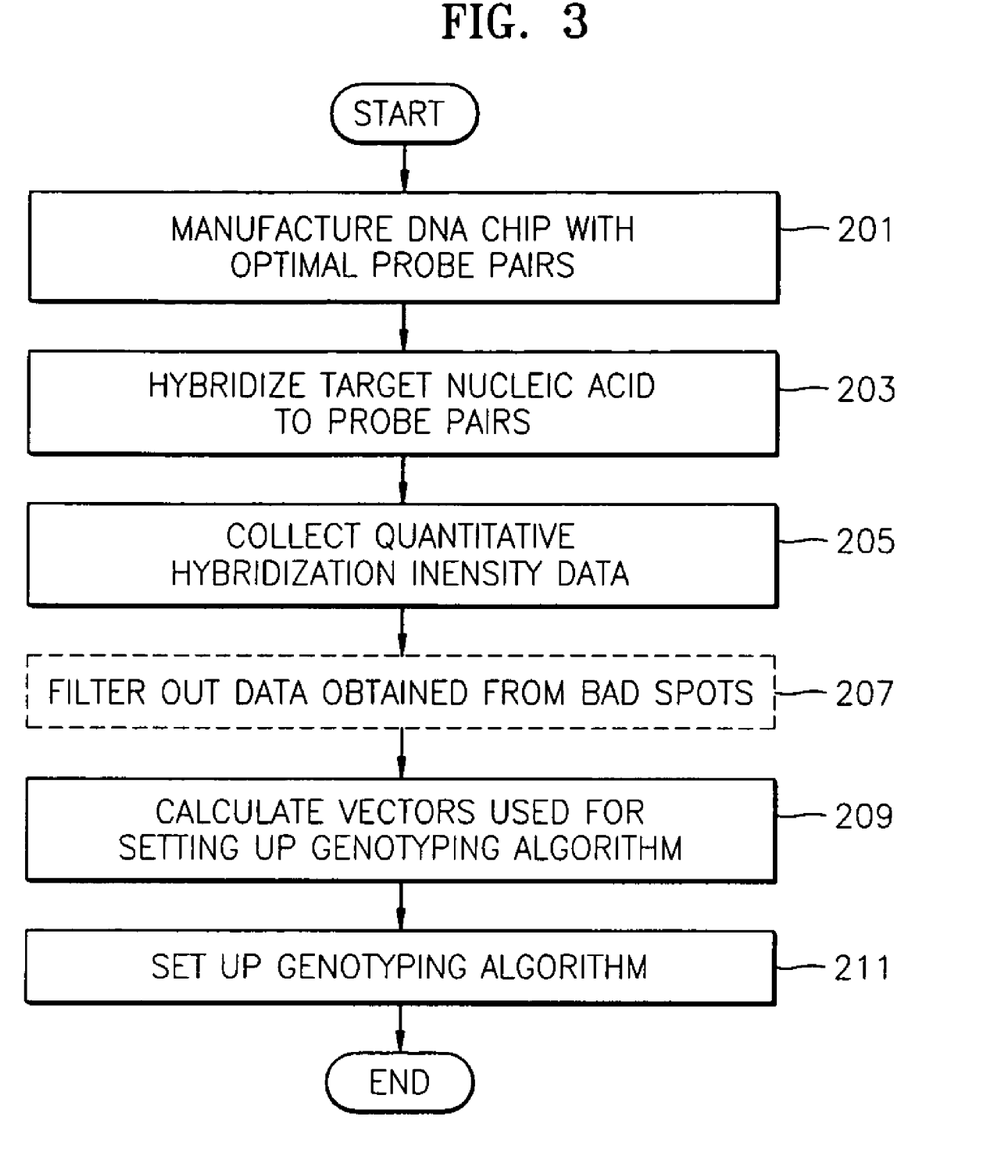
FIG. 3 is a flowchart of the step of setting up a genotyping algorithm.

Referring to FIG. 3, which is a detailed flowchart of the setting up of the genotyping algorithm in step 200 in FIG. 1, a DNA chip is manufactured by arranging the optimal probe pairs for the respective mutation sites in a microarray (step 201). This DNA chip may be manufactured by the same method applied to the manufacture of the optimal probe pair screening chip. It is preferable that at least two identical optimal probe pairs are arranged for each of the mutation sites for quality control (QC) and quality assurance (QA). It is more preferable that at least two wp probes are arranged side by side and at least two mp probes are arranged side by side adjacent to the wp probes for each of the mutation sites to allow visual identification of the hybridized results. It is most preferable that three wp probes are arranged side by side and three mp probes are arranged side by side adjacent to the wp probes for each of the mutation sites in terms of QC, QA, and costs.

Next, after the target nucleic acid is hybridized to the chip (step 203), quantitative hybridization intensity data are collected by means of a scanner (step 205). After hybridization, the chip is washed prior to collecting the quantitative hybridization intensity data.

Data obtained from bad spots among the quantitative hybridization intensity data may be filtered out (step 207). Criteria for bad spot discrimination include an effective spot diameter cutoff value, an effective spot intensity cutoff value, etc., which can be calculated based on a number of statistical data. In an embodiment of the present invention, spots that have a larger diameter than an effective spot diameter are eliminated as bad spots for statistical data analysis.

Next, vectors for the genotyping algorithm are calculated using the quantitative hybridization intensity data (step 209). These vectors may be calculated using Hodge-lehman (H-L) estimation that is a typical method applied in nonparametric statistics to raise the roboustness of the genotyping algorithm. The vectors used to set up the genotyping algorithm in the present invention include ratio components and/or intensity components.

Ratio components are calculated as follows.

The ratio between the hybridization intensity of a nucleic acid to a wild-perfect match probe ($wp_i$) and the hybridization intensity of the nucleic acid to a mutant-perfect match probe ($mp_j$) is calculated for all of the probe pairs, where i×j=n, as expressed in equation (2) below.

$$r_{ij} = \frac{\text{Hybridization Intensity to } wp_i}{\text{Hybridization Intensity to } mp_j} \quad (2)$$

After calculating the ratios $r_{ij}$ for all of the probe pairs, the ratios $r_{ij}$ are arranged in ascending order, for example, r(1) .r(2), . . . , r(n−1) .r(n), and the median, r(m), is selected from among the ratios.

For example, when three wp probes and three mp probes are arranged at a mutation site, the ratios for a total of nine wp-mp probe pairs are calculated and arranged in ascending order, i.e., r(1) ., . . . , .r(5) ., . . . , r(9), and r(5) is selected as the median r(m).

The natural logarithm of the median r(m), expressed in equation (3) below, is used as a ratio component.

$$M = \text{Ratio component} = \ln(r(m)) \quad (3)$$

Alternatively, the common logarithm (log) of the median r(m) instead of the natural logarithm (ln) may be used as the ratio component.

The use of the median results in a genotyping algorithm that is more robust to experimental errors than using the arithmetic means of the hybridization intensities of the probes for each mutation site. For example, when the hybridization intensity of mp3 greatly deviates from the hybridization intensities of mp1 and mp2, as in Table 1 below, calculating the median using H-L estimation as a ratio component leads to a result that is more robust to experimental errors than calculating the arithmetic means.

TABLE 1

| Probe ID. | Hybridization Intensity |
| --- | --- |
| E04-22-wp1 | 948 |
| E04-22-wp2 | 870 |
| E04-22-wp3 | 1071 |
| E04-22-mp1 | 74 |
| E04-22-mp2 | 73 |
| E04-22-mp3 | 1363 |

Intensity components are calculated as follows.

A first method involves multiplying the hybridization intensities of each of the wp-mp probe pairs to obtain the products $a_{ij}$, as expressed in equation (4) below, where i×j=n.

$$a_{ij} = wp_i \times mp_j \quad (4)$$

After calculating the products $a_{ij}$ for all of the wp-mp probe pairs, the median a(m) among the products $a_{ij}$ is selected using H-L estimation in the same manner as described above.

The natural logarithm of the median a(m) is divided by two to obtain an intensity component A, as expressed in equation (5) below.

$$A = \text{Intensity component} = \ln(a(m))/2 \quad (5)$$

A second method involves taking the larger of the hybridization intensities of each of the wp-mp probe pairs, as expressed in equation (6) below.

$$m_{ij} = \max(wp_i, mp_j) \quad (6)$$

The median m(m) is selected from among $m_{ij}$ and the common logarithm of the median m(m) is used as an intensity component A, as expressed in equation (7) below.

$$A = \text{Intensity component} = \log(m(m)) \quad (7)$$

The common logarithm may be applied instead of the natural logarithm in equation (5). The natural logarithm may be applied instead of the common logarithm in equation (7).

Steps 203 through 209 are performed using a plurality of chips to obtain a plurality of ratio components M and intensity components A.

The vectors consisting of the ratio components M and the intensity components A, which are obtained based on the hybridization intensity data according to the above-described methods, are used to set up the genotyping algorithm (step 211).

To set up the genotyping algorithm, an MA plot with the Y and X axes parameterized by the ratio (M) and intensity (A) components, respectively, is obtained.

Figure 4:
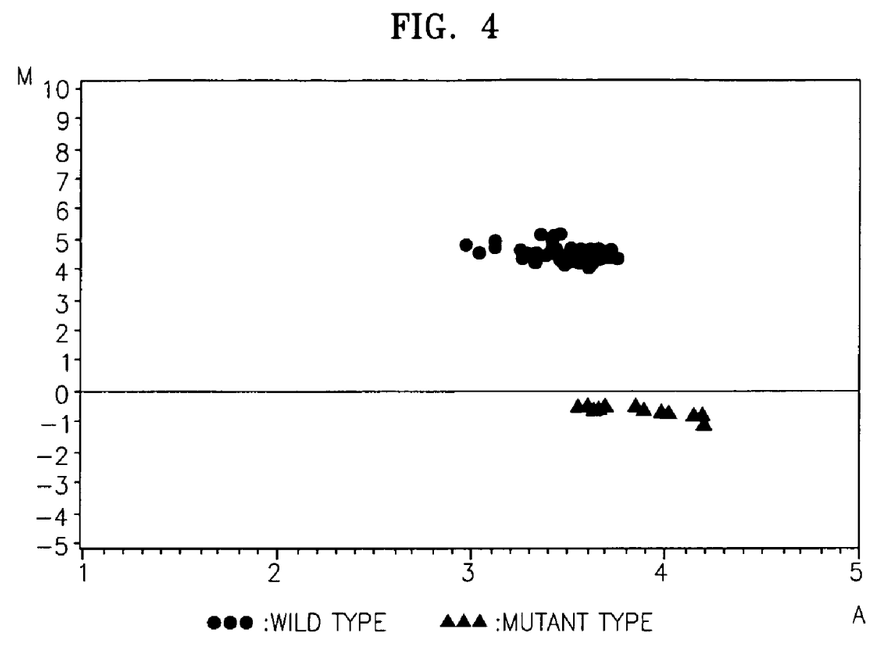
FIG. 4 is a graph of ratio component (M) versus intensity component (A) used in setting up a genotyping algorithm for position 1 of exon 2 (E02-01) of MODY2 alpha 1 gene.

FIG. 4 is an MA plot used in setting up a genotyping algorithm for position 1 of exon 2 (E02-01) of MODY2 alpha 1 gene. The MA plot of FIG. 4 was obtained through the following processes.

First, an array of probes were immobilized on a glass substrate to manufacture a complete chip such that three wp probes and three mp probes, which had been designed to detect E02-01 of the gene, were positioned side by side on the glass substrate. A spotting solution of E02-01 wp and E02-01 mp probes with amine groups dispersed in a hydrogel prepared from a polyethyleneglycol (PEG) derivative with epoxy groups was used to manufacture the chip. The spotting solution was spotted onto an aminated surface of the glass substrate using a biorobot printer (PixSys 5500, Cartesian Technologies InC., CA, U.S.A.) and incubated in a humid incubator at 37. for 4 hours. To control background noise, amine groups in a non-spotting region of the glass substrate were reacted to be negatively charged to prevent standard nucleic acids from binding to the non-spotting region of the substrate and then stored in a drier.

The standard nucleic acid was fluorescently labelled. Available fluorescent materials include fluorescein isothiocyanate (FITC), fluorescein, Cy3, Cy5, Texas Red, and the like. In the experiment regarding the MA plot of FIG. 4, Cy3-dUTP was used as the fluorescent material.

The standard nucleic acid was hybridized to the probes as follows. A 20 nM standard nucleic acid solution in 0.1% 6SSPET (saline sodium phosphate EDTA buffer containing 0.1% Trition X-100) was reacted with the chip at 37. for 16 hours, dried at room temperature for 5 minutes, and scanned using an Axon scanner (GenePix 4000B, Axon Instrument Inc., CA., U.S.A.). The resulting scanning data were analyzed using software (GenePix Pro 3.0, Axon Instrument Inc., CA., U.S.A.) to calculate ratio and intensity components and plot FIG. 4. The scanning data were obtained through hybridization with a wild type standard nucleic acid using 100 chips and through hybridization with a mutant type standard nucleic acid using 30 chips.

When the ratio component M remains constant as the intensity component A varies, as in FIG. 4, a genotyping algorithm is set up using only the ratio component M. The genotyping algorithm may be set up using logistic regression coefficients a and b predicted by logistic regression.

However, when the ratio component M has a strong dependence on the intensity component A, for example, when the ratio component M decreases with decreasing intensity component A, the genotyping algorithm may be set up according to one of the following methods. In one method, a set of probes with the ratio components that decrease with decreasing intensity components is disregarded when calculating the logistic regression coefficients a and b using logistic regression. In another method, the genotyping algorithm may be set up based on a 2-dimensional vector matrix of probes' ratio components and intensity components. However, the former is preferred to the latter in consideration of inherent great intensity variations in the DNA chip.

Genotyping

After the genotyping algorithm is set up through the above processes, genotyping is performed on a target nucleic acid of interest. Input vectors for the genotyping algorithm set up in step 211 are calculated based on the results of a test performed on the target nucleic acid using the DNA chip.

Figure 5:
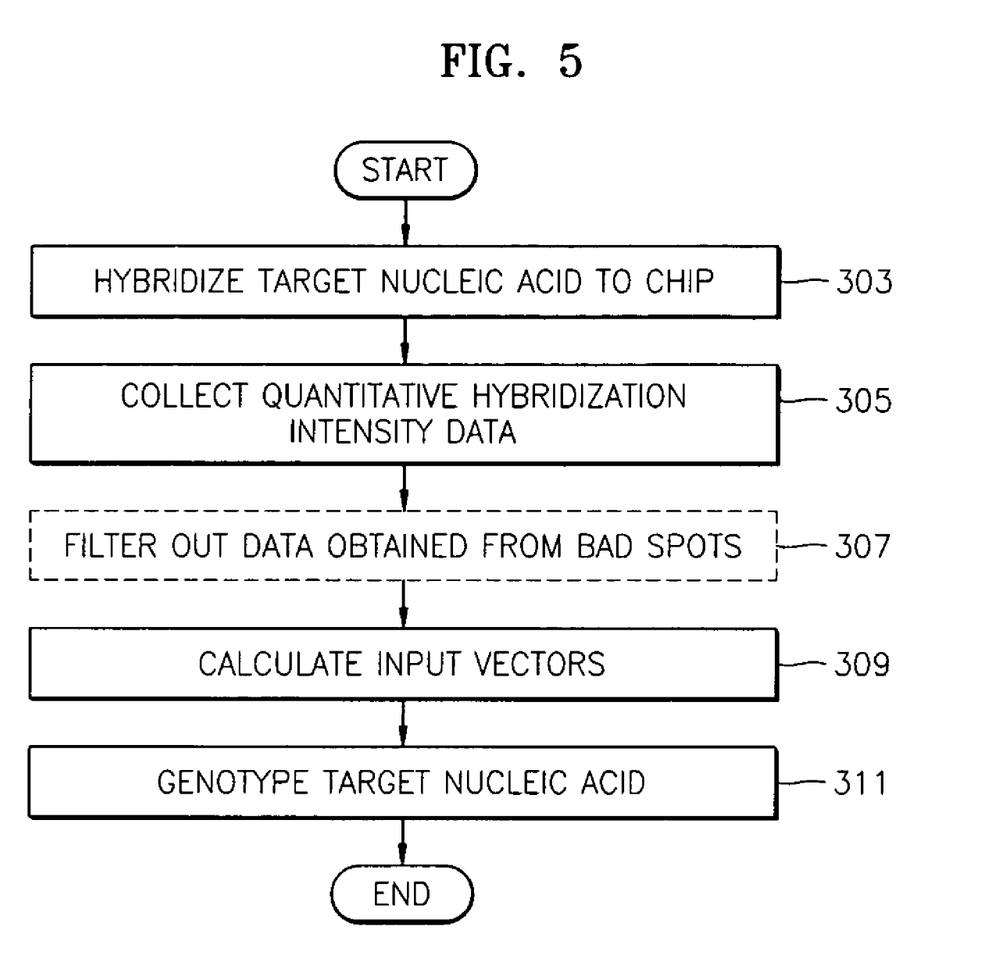
FIG. 5 is a detailed flowchart of a genotyping step.

FIG. 5 is a detailed flowchart of a genotyping process. Up to the step of calculating the input vectors is performed in the same manner as in step 211 of setting up the genotyping algorithm. In particular, the target nucleic acid of interest is hybridized to the chip with which the genotyping algorithm has been set up (step 303). Next, quantitative hybridization intensity data regarding the target nucleic acid are collected (step 305). Optionally, data obtained from bad spots may be filtered out from the quantitative hybridization intensity data (step 307).

Next, the input vectors for the genotyping algorithm are calculated based on the quantitative hybridization intensity data (step 309). Ratio components are calculated using H-L estimation as in step 211. When an MA plot is required as in step 211, intensity components as well as the ratio components are calculated.

The genotype of the target nucleic acid is identified using the genotyping algorithm with the input vectors (step 311). The genotyped results for the target nucleic acid and the standard nucleic acid may be plotted together on the same MA graph for comparative visual identification.

Figure 6:
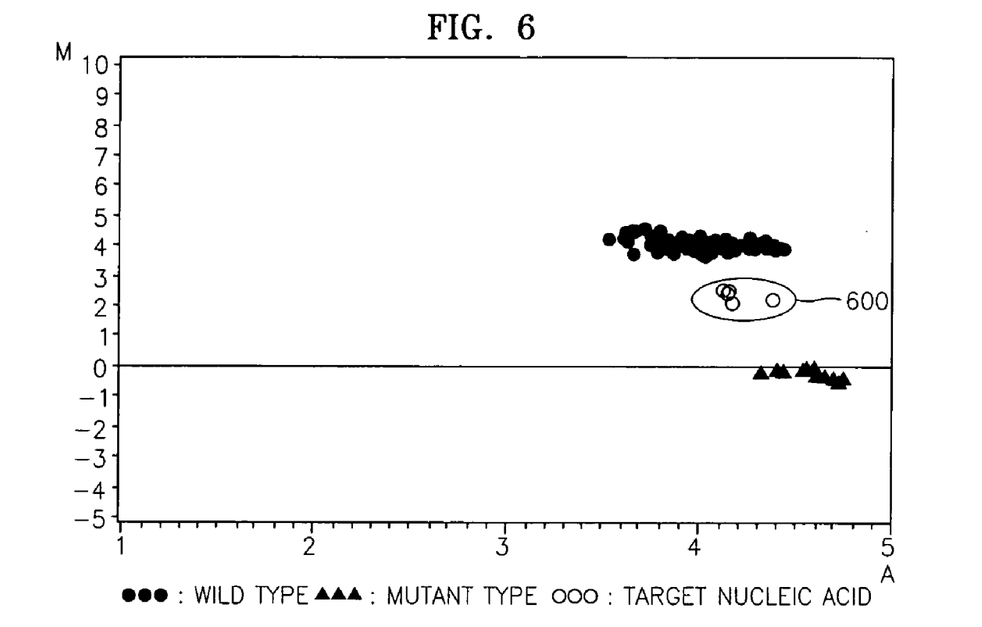
FIG. 6 is an MA plot used in setting up a genotyping algorithm for mutation site 18 of exon 4 (E04-18) of MODY2 alpha 1 gene, in which the results of genotyping an unidentified target nucleic acid are also plotted.

FIG. 6 is an MA plot used in setting up a genotyping algorithm for mutation site 18 of exon 4 (E04-18) of MODY2 alpha 1 gene, in which the results of genotyping an unidentified target nucleic acid are also plotted. The MA plot of FIG. 6 was obtained in the same manner as for the MA plot of FIG. 4. The genotyped results of the target nucleic acid are circled with reference numeral 600. It has to be identified whether the target nucleic acid is a wild type or a mutant type.

This genotyping process is performed as follows. Initially, ratio components m for the target nucleic acid that belong to circle 600 are substituted as input vectors into the genotyping algorithm with the estimated logistic regression coefficients a and b and the posterior probabilities that the target nucleic acid is a wild type or a mutant type are calculated as follows.

$$P(\text{wild}|m) = \exp(a+bm)/\{1+\exp(a+bm)\}$$

$$P(\text{mutant}|m) = 1/\{1+\exp(a+bm)\} = 1 - P(\text{wild}|m)$$

The genotype of the target nucleic acid is determined according to the greater of the two posterior probabilities. It is preferable that provisional genotyping with the greater posterior probability is followed by reliability validation on the greater posterior probability at a particular significance level. In this case, if the reliability requirement is not satisfied, genotyping of the target nucleic acid is deferred. In the reliability test, a confidence interval of the maximal posterior probability at the particular significance level is calculated. If the confidence interval includes 0.5, no genotyping of the target nucleic acid is performed and the target nucleic acid is assigned as a gray zone. A method of calculating the confidence interval of the greater posterior probability is described in detail in Chapter 1 of *Applied Logistic Regression* (Hosmer, D. W., Jr. and Lemeshow, S, John Wiley & Sons Inc., 1989), incorporated herein by reference in its entirety. Genotyping criteria may be more restricted by using a value that is greater than 0.5, for example, 0.7, in the reliability test. However, if the genotyping is deferred too frequently, then the DNA chip does not work properly. Therefore, it is required to establish optimal genotyping criteria in consideration of the no-genotyping rate and the mis-genotyping rate.

When there are a set of probes with the ratio components M that decrease with decreasing intensity components A, those ratio components are eliminated so that the remaining ratio components are used as a learning set. When a genotyping algorithm with logistic regression coefficients that are calculated using the learning set is used, genotyping of a target nucleic acid may be deferred if the result of hybridisation of the target nucleic acid is within an intensity domain with smaller ratio components.

Correction of Genotyped Results

After genotyping through the above-described processes, the genotyped results are corrected to minimize errors in deferring genotyping. The genotyped results may be corrected based on the result of cross-hybridization. For example, when it is known that a mutant type target nucleic acid may cross-hybridize to a probe pair that is irrelevant to the identification of the mutation site of the target nucleic acid, the genotyped results can be corrected using the cross-hybridization information on the target nucleic acid.

Figure 7:
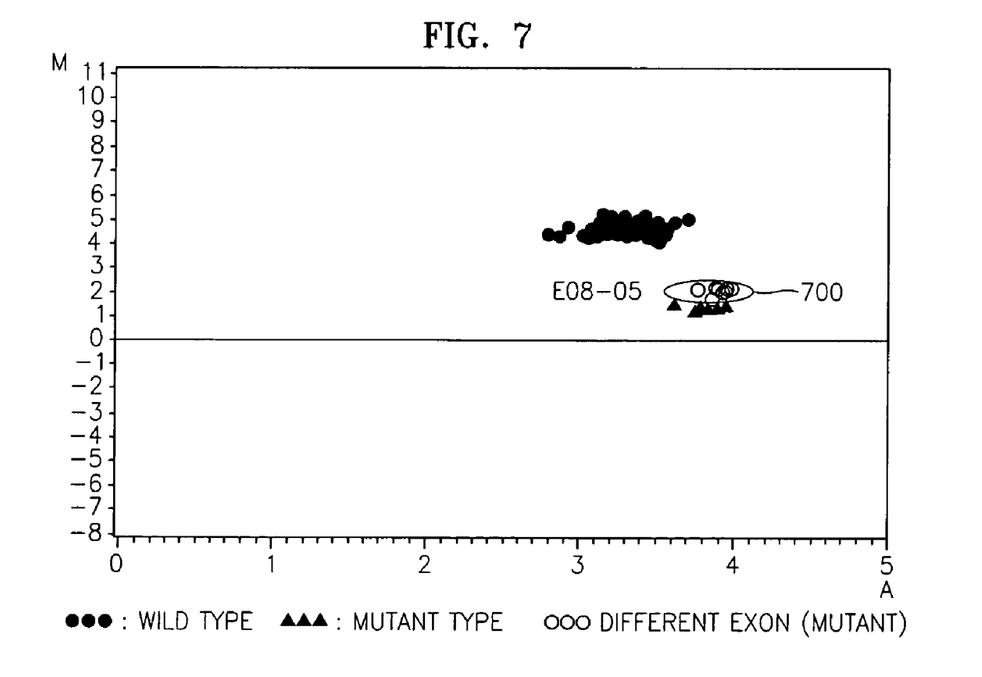
FIGS. 7 and 8 are MA plots for explaining correcting genotype results using cross-hybridization information of probe pairs.
Figure 8:
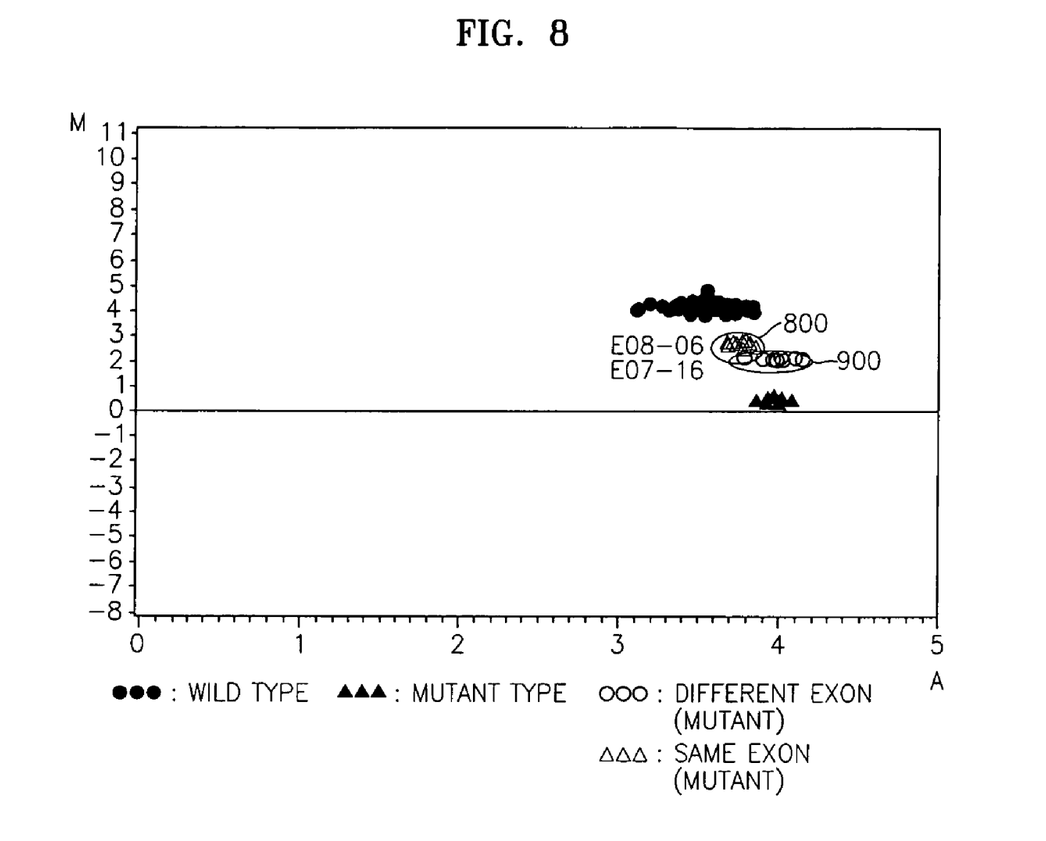

An example of correcting the genotyped results of a nucleic acid will be described with reference to FIGS. 7 and 8. The experimental results in FIGS. 7 and 8 were obtained using the same method as applied to obtain the results in FIG. 4. FIG. 7 is an MA plot illustrating a case where a wild type gene was erroneously identified as a mutant type. FIG. 8 is an MA plot illustrating a case where genotyping of a gene that is known to be a wild type was deferred.

In particular, FIG. 7 is an MA plot illustrating the results of hybridization between E07-16 probe pairs, which are designed to genotype position 16 of exon 7 (E07-16) of MODY2 alpha 1 gene, and a standard nucleic acid that is identified as carrying a mutation at position 5 of exon 8 (E08-05). In FIG. 7, . denotes the results of hybridization between an wild type standard nucleic acid and the E07-16 probe pairs, ▼ denotes the results of hybridization between an E07-16 mutant type standard nucleic acid and the same probe pairs, and ○ (reference numeral 700) denotes the results of hybridization between the E08-05 mutant type standard nucleic acid and the probe pairs. As is apparent from the MA plot of FIG. 7, the E08-05 mutant type standard nucleic acid may be mistakenly identified as an E07-16 mutant type nucleic acid due to the cross-hybridization with the E07-16 probe pairs.

FIG. 8 is an MA plot illustrating the results of hybridization between E08-05 probe pairs, which are designed to identify whether there is a mutation at position 5 of exon 8 (E08-05) of MODY2 alpha gene, and a E07-16 mutant type standard nucleic acid and the results of hybridization between the E08-05 probe pairs and a E08-06 mutant type standard nucleic acid. In FIG. 8, . denotes the results of hybridization between a wild type standard nucleic acid and the E08-05 probe pairs, ▼ denotes the results of hybridization between a E08-05 mutant type standard nucleic acid and the same probe pairs, (reference numeral 800) denotes the results of hybridization between the E08-06 mutant type standard nucleic acid and the probe pairs, and ○ (reference numeral 700) denotes the results of hybridization between the E07-16 mutant type standard nucleic acid and the probe pairs. As is apparent from the MA plot of FIG. 8, genotyping of the target nucleic acid at E08-05 mutation site may be deferred due to the cross-hybridization between the E08-05 probe and both the E08-06 mutant type standard nucleic acid and the E07-16 mutant type standard nucleic acid.

In other words, if the fact that an E08-05 mutant type nucleic acid may be erroneously identified as an E07-16 mutant type nucleic acid, as in the case of FIG. 7, and the fact that genotyping of an E08-05 mutant type nucleic acid may be deferred due to the cross-hybridization of an E07-16 mutant type nucleic acid to E08-05 probe pairs, as in the case of FIG. 8, are known before hybridization of the E08-05 mutant type target nucleic acid, the genotyped results of the target nucleic acid can be corrected as follows.

In particular, when the target nucleic acid is identified as carrying mutations at both positions E08-05 and E07-16 based on the results of hybridization to the chip, the genotyped result regarding the mutation at position E07-16, which results from cross-hybridization, is corrected so that the genotype of the target nucleic acid at E07-16 is identified as a wild type. When the genotype of the target nucleic acid at E07-16 position is identified as a mutant type and genotyping of E08-05 position of the target nucleic acid is deferred, based on the results of hybridization to the chip, the genotyped results are corrected so that the genotype of the target nucleic acid at E08-05 is identified as a wild type.

When it is known that E07-16 mutant type nucleic acids and E-08-06 mutant type nucleic acid may cross-hybridize to E08-05 probe pairs, as in FIG. 8, which forces a deferral of a determination of the genotype of the target nucleic acid, and that such cross-hybridization does not occur with E8-06 probe pairs, the genotyped results of the target nucleic acid can be corrected as follows. That is, when the target nucleic acid is determined as carrying a mutation at E08-06 and genotyping of E08-05 position of the target nucleic acid is deferred, the genotyped results are corrected as the genotype of the target nucleic acid at E08-05 being a wild type.

As described above, a genotyping method according to the present invention is robust to errors. Optimal probe pairs for each mutation site are selected to minimize genotyping errors. In addition, input vectors for the genotyping algorithm are calculated using H-L estimation, which is a statistical technique known to be robust to experimental errors, thereby minimizing genotyping errors. In an important test in which high accuracy is required, genotyping accuracy can be improved by applying more restricted genotyping criteria.

Chip's quality control and quality assurance are ensured with the genotyping method according to the present invention. Since a plurality of identical probes are immobilized on a chip used in the genotyping method according to the present invention, outlier data can be filtered out based on variations in data obtained from a plurality of identical probes. Also, criteria for screening failed chips can be established based on the experimental results obtained in a genotyping algorithm set-up process through repeated hybridization between wild type standard nucleic acids and all probes that perfectly match the wild type standard nucleic acid.

The genotyped results of a target nucleic acid can be corrected based on the cross-hybridization patterns of probe pairs immobilized for each mutation site in a chip to identify the target nucleic acid. Since at least two replicates of optimal probe pair are immobilized for each mutation site of the chip in the present invention, it is easy to obtain more accurate cross-hybridization data. Thus, when a genotyped result is incorrect, such as when genotyping of a target nucleic acid that is known to be a wild type is deferred or when a wild type target nucleic acid is genotyped as a mutant type, the mis-genotyped result can be corrected based on the cross-hybridization information.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A genotyping method comprising
   hybridizing a target nucleic acid to a DNA chip on which an optimal probe pair is immobilized,
   wherein the optimal probe pair consists of a wild type-perfect match probe for a mutation site on the target nucleic acid and a mutant type-perfect match probe for the mutation site,
   wherein the optimal probe pair is selected by:
   designing a plurality of probe pairs for the mutation site, wherein a probe pair consists of a wild type-perfect match probe and a mutant type-perfect match probe;
   immobilizing the plurality of probe pairs on a substrate to manufacture an optimal probe pair screening chip;
   hybridizing a standard nucleic acid to the optimal probe pair screening chip;
   collecting quantitative hybridization intensity data;
   calculating a value for each probe pair of the following equation;

$$\{\text{Mean}(\ln(r^{wt})) - 2\ \text{SD}(\ln(r^{wt}))/<\sqrt{N^{wt}}\} - \{\text{Mean}(\ln(r^{mt})) + 2\text{SD}(\ln(r^{mt}))/\sqrt{N^{mt}}\}$$

wherein N denotes a number of times hybridization of the standard nucleic acid has been performed;
   $r^{wt}$ is a ratio between a hybridization intensity of a wild type standard nucleic acid to the wild type-perfect match probe and a hybridization intensity of the wild type standard nucleic acid to the mutant type-perfect match probe;
   $r^{mt}$ is a ratio between a hybridization intensity of a mutant type standard nucleic acid to the wild type-perfect match probe and a hybridization intensity of the mutant type standard nucleic acid to the mutant type-perfect match probe; and
   Mean and SD denote a mean value and a standard deviation, respectively, of N ln(r) values, which are obtained by hybridizing the standard nucleic acid to the DNA chip N times; and
   selecting the probe pair having the largest value as the optimal probe pair.

2. The genotyping method of claim 1, wherein at least two optimal probe pairs for the mutation site are immobilized on the DNA chip.

3. The genotyping method of claim 2, wherein at least two wild type-perfect match probes for the mutation site are arranged side by side and at least two mutant type-perfect match probes for the mutation site are arranged side by side adjacent to the wild type-perfect match probes on the DNA chip.

4. The genotyping method of claim 1, further comprising:
   (a) setting up a genotyping algorithm for hybridization of a standard nucleic acid to the DNA chip; and
   (b) genotyping the target nucleic acid by substituting an input vector that is calculated from hybridization of the target nucleic acid to the DNA chip into the genotyping algorithm.

5. The genotyping method of claim 4, wherein (a) comprises:
   (a-1) collecting quantitative hybridization intensity data obtained from hybridization of the standard nucleic acid to the DNA chip;
   (a-2) calculating a ratio, $r_{ij}$, for every pairing of a wild type-perfect match probe ($wp_i$) of an optimal probe pair (i) immobilized on the DNA chip for the mutation site on the target nucleic acid and a mutant type-perfect match probe ($mp_j$) of an optimal probe pair (j) immobilized on the DNA chip for the mutation site on the target nucleic acid, wherein the ratio, $r_{ij}$, is between a hybridization intensity of the standard nucleic acid to the wild type-perfect match probe ($wp_i$) and a hybridization intensity of the standard nucleic acid to the mutant type-perfect match probe ($mp_j$), selecting a Hodge-Lehman median from among the calculated ratios, and taking the logarithm of the median as a ratio component of a vector for the DNA chip; and (a-3) repeating (a-1) and (a-2) with a plurality of DNA chips to obtain ratio components for a set of vectors.

6. The genotyping method of claim 5, wherein (a-3) further comprises calculating logistic regression coefficients for the set of vectors.

7. The genotyping method of claim 5, wherein (a-2) further comprises obtaining a product, $a_{ij}$, for every pairing of a wild type-perfect match probe ($wp_i$) of an optimal probe pair (i) immobilized on the DNA chip for the mutation site on the target nucleic acid and a mutant type-perfect match probe ($mp_j$) of an optimal probe pair (j) immobilized on the DNA chip for the mutation site on the target nucleic acid, wherein the product, $a_{ij}$, is obtained by multiplying the hybridization intensity of the standard nucleic acid to the wild type-perfect match probe ($wp_i$) and the hybridization intensity of the standard nucleic acid to the mutant type-perfect match probe ($mp_j$), selecting the Hodge-Lehman median from among the products, dividing the logarithm of the median by two to obtain an intensity component of the vector for the DNA chip;

wherein the genotyping method further comprises plotting a graph with the Y-axis parameterized by the ratio component and the X-axis parameterized by the intensity component before (a-3); and the genotyping algorithm comprises logistic regression coefficients of all of the ratio components if the ratio components are independent of the intensity components or comprises logistic regression coefficients of only the ratio components which are independent of the intensity components if the ratio components are dependent on the intensity components.

8. The genotyping method of claim 5, wherein (a-2) further comprises comparing, for every pairing of a wild type-perfect match probe ($wp_i$) of an optimal probe pair (i) immobilized on the DNA chin for the mutation site on the target nucleic acid and a mutant type-perfect match probe ($mp_j$) of an optimal probe pair (j) immobilized on the DNA chip for the mutation site on the target nucleic acid, the hybridization intensity of the standard nucleic acid to the wild type-perfect match probe ($wp_i$) and the hybridization intensity of the standard nucleic acid to the mutant type-perfect match probe ($mp_j$), to determine which is the larger, selecting the Hodge-Lehman median from among the larger hybridization intensities, taking the logarithm of the median as an intensity component of the vector-for the DNA chip;

the genotyping method further comprises plotting a graph with the Y-axis parameterized by the ratio component and the X-axis parameterized by the intensity component before (a-3); and the genotyping algorithm comprises logistic regression coefficients of all of the ratio components if the ratio components are independent of the intensity components or comprises logistic regression coefficients of only the ratio components which are independent of the intensity components if the ratio components are dependent on the intensity components.

9. The genotyping method of claim 5, further comprising filtering quantitative hybridization intensity data obtained from bad spots from the quantitative hybridization intensity data collected in step (a-1) before (a-2), wherein a bad spot on the DNA chip has a larger diameter than an effective spot diameter.

10. The genotyping method of claim 4, wherein (b) comprises:

(b-1) collecting quantitative hybridization data obtained from hybridization of the target nucleic acid to the DNA chip;

(b-2) calculating a ratio $r_{ij}$, for every pairing of a wild type-perfect match probe ($wp_i$) of an optimal probe pair (i) immobilized on the DNA chip for the mutation site on the target nucleic acid and a mutant type-perfect match probe ($mp_j$) of an optimal probe pair (j) immobilized on the DNA chip for the mutation site on the target nucleic acid, wherein the ratio, $r_{ij}$, between a hybridization intensity of the target nucleic acid to the wild type-perfect match probe ($wp_i$) and a hybridization intensity of the target nucleic acid to the mutant type-perfect match probe ($mp_j$), selecting the Hodge-Lehman median from among the calculated ratios, and taking the logarithm of the median as an input vector for genotyping; and (b-3) substituting the input vector into the genotyping algorithm to genotype the target nucleic acid.

11. The genotyping method of claim 10, wherein (b-3) comprises calculating a posterior probability that the target nucleic acid is a wild type and a posterior probability that the target nucleic acid is a mutant type by substituting the input vector into the genotyping algorithm and detennimng the genotype of the target nucleic acid to be a wild type if the posterior probability that the target nucleic acid is a wild type is greater than the posterior probability that the target nucleic acid is a mutant type or deterniining the genotype of the target nucleic acid to be a mutant type if the posterior probability that the target nucleic acid is a wild type is less than the posterior probability that the target nucleic acid is a mutant.

12. The genotyping method of claim 11, wherein (b-3) further comprises:

validating the genotype determination based on a reliability requirement, wherein the reliability requirement is that the posterior probability of the determined genotype be at a predetermined significance level and deferring determination of a genotype of the target nucleic acid if the reliability requirement is not satisfied.

13. The genotyping method of claim 10, further comprising filtering quantitative hybridization intensity data obtained from bad spots from the quantitative hybridization intensity data collected in step (b-1) before (b-3), wherein a bad spot on the DNA chip has a larger diameter than an effective spot diameter.

14. The genotyping method of claim 4, further comprising correcting the genotyped results from step (b).

* * * * *